(12) United States Patent
Richard et al.

(10) Patent No.: US 10,561,418 B2
(45) Date of Patent: *Feb. 18, 2020

(54) ADAPTER ASSEMBLIES FOR INTERCONNECTING SURGICAL LOADING UNITS AND HANDLE ASSEMBLIES

(71) Applicant: Covidien LP, Mansfield, MA (US)

(72) Inventors: Paul Richard, Shelton, CT (US); Earl M. Zergiebel, Guilford, CT (US); David M. Chowaniec, Rocky Hill, CT (US); Ryan V. Williams, New Hartford, CT (US); Anand Subramanian, Stamford, CT (US); Nihir Patel, Stamford, CT (US)

(73) Assignee: Covidien LP, Mansfield, MA (US)

( * ) Notice: Subject to any disclaimer, the term of this patent is extended or adjusted under 35 U.S.C. 154(b) by 1122 days.

This patent is subject to a terminal disclaimer.

(21) Appl. No.: 14/700,605

(22) Filed: Apr. 30, 2015

(65) Prior Publication Data
US 2015/0374371 A1 Dec. 31, 2015

Related U.S. Application Data

(60) Provisional application No. 62/017,626, filed on Jun. 26, 2014.

(51) Int. Cl.
*A61B 17/072* (2006.01)
*A61B 17/00* (2006.01)
(Continued)

(52) U.S. Cl.
CPC ........ *A61B 17/07207* (2013.01); *A61B 90/90* (2016.02); *A61B 90/98* (2016.02);
(Continued)

(58) Field of Classification Search
None
See application file for complete search history.

(56) References Cited

U.S. PATENT DOCUMENTS

| 2,777,340 A | 1/1957 | Hettwer et al. |
| 2,957,353 A | 10/1960 | Babacz |

(Continued)

FOREIGN PATENT DOCUMENTS

| AU | 2008229795 A1 | 4/2009 |
| CA | 2451558 A1 | 1/2003 |

(Continued)

OTHER PUBLICATIONS

Extended European Search Report corresponding to International Application No. EP 15 15 1076.5 dated Apr. 22, 2015.

(Continued)

*Primary Examiner* — Michelle Lopez
*Assistant Examiner* — Chinyere J Rushing-Tucker

(57) ABSTRACT

An adapter assembly includes an elongated body, a switch, a sensor link, and an annular member. The elongated body includes a proximal portion configured to couple to a handle assembly and a distal portion configured to couple to a surgical loading unit. The switch is configured to be toggled in response to the surgical loading unit being coupled to the distal portion of the adapter assembly. The sensor link is disposed within the distal portion of the adapter assembly and biased toward a distal position. The sensor link is longitudinally movable between a proximal position and the distal position. The annular member is disposed within the distal portion and is rotatable between a first orientation, in which the annular member prevents distal movement of the sensor link, and a second orientation, in which the sensor link moves distally to toggle the switch.

9 Claims, 14 Drawing Sheets

(51) Int. Cl.
  *A61B 90/90* (2016.01)
  *A61B 90/98* (2016.01)
  *A61B 90/00* (2016.01)

(52) U.S. Cl.
  CPC ............... *A61B 2017/0046* (2013.01); *A61B 2017/00221* (2013.01); *A61B 2017/00398* (2013.01); *A61B 2017/00473* (2013.01); *A61B 2090/0803* (2016.02); *A61B 2090/0808* (2016.02)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| RE34,556 E | 3/1994 | Sjostrom et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,122 A | 7/2000 | Sjostrom et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |

(56) References Cited

U.S. PATENT DOCUMENTS

| | | |
|---|---|---|
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,887,559 B2 | 2/2011 | Deng et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |

(56) References Cited

U.S. PATENT DOCUMENTS

| | | |
|---|---|---|
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0320252 A1 | 12/2010 | Viola et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1* | 4/2012 | Zemlok ............ A61B 17/07207 606/1 |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0092719 A1* | 4/2013 | Kostrzewski .... A61B 17/07207 227/177.1 |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0053749 A1* | 2/2015 | Shelton, IV ......... A61B 17/068 227/181.1 |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0173747 A1* | 6/2015 | Baxter, III et al. ......... A61B 17/07207 227/177.1 |
| 2015/0216525 A1* | 8/2015 | Collins .................... H05K 7/06 227/176.1 |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0100839 A1* | 4/2016 | Marczyk .......... A61B 17/07207 227/175.3 |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2462878 A1 | 6/2012 |
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |

(56) References Cited

FOREIGN PATENT DOCUMENTS

| | | |
|---|---|---|
| ES | 2333509 A1 | 2/2010 |
| JP | 08-038488 | 2/1996 |
| JP | 2005-125075 A | 5/2005 |
| KR | 20120022521 A | 3/2012 |
| WO | 99/15086 A1 | 4/1999 |
| WO | 2000/072760 A1 | 12/2000 |
| WO | 2000/072765 A1 | 12/2000 |
| WO | 2003/000138 A2 | 1/2003 |
| WO | 2003/026511 A1 | 4/2003 |
| WO | 2003/030743 A2 | 4/2003 |
| WO | 2003065916 A1 | 8/2003 |
| WO | 2003/077769 A1 | 9/2003 |
| WO | 2003/090630 A2 | 11/2003 |
| WO | 2004/107989 A1 | 12/2004 |
| WO | 2006/042210 A2 | 4/2006 |
| WO | 2007016290 A2 | 2/2007 |
| WO | 2007/026354 A1 | 3/2007 |
| WO | 2007137304 A2 | 11/2007 |
| WO | 2008/131362 A2 | 10/2008 |
| WO | 2008/133956 A2 | 11/2008 |
| WO | 2009/039506 A1 | 3/2009 |
| WO | 2007014355 A3 | 4/2009 |
| WO | 2009/132359 A2 | 10/2009 |
| WO | 2009/143092 A1 | 11/2009 |
| WO | 2009/149234 A1 | 12/2009 |
| WO | 2011/108840 A2 | 9/2011 |
| WO | 2012040984 A1 | 4/2012 |

OTHER PUBLICATIONS

Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.

* cited by examiner

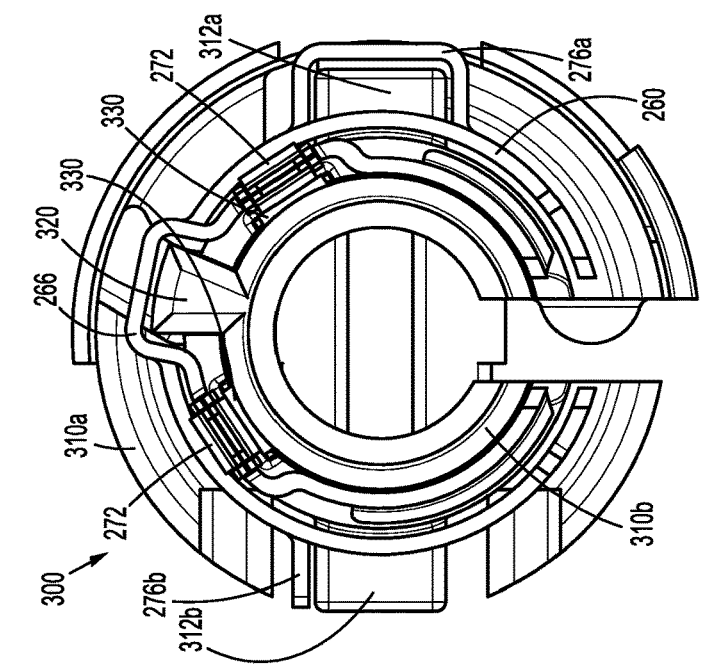
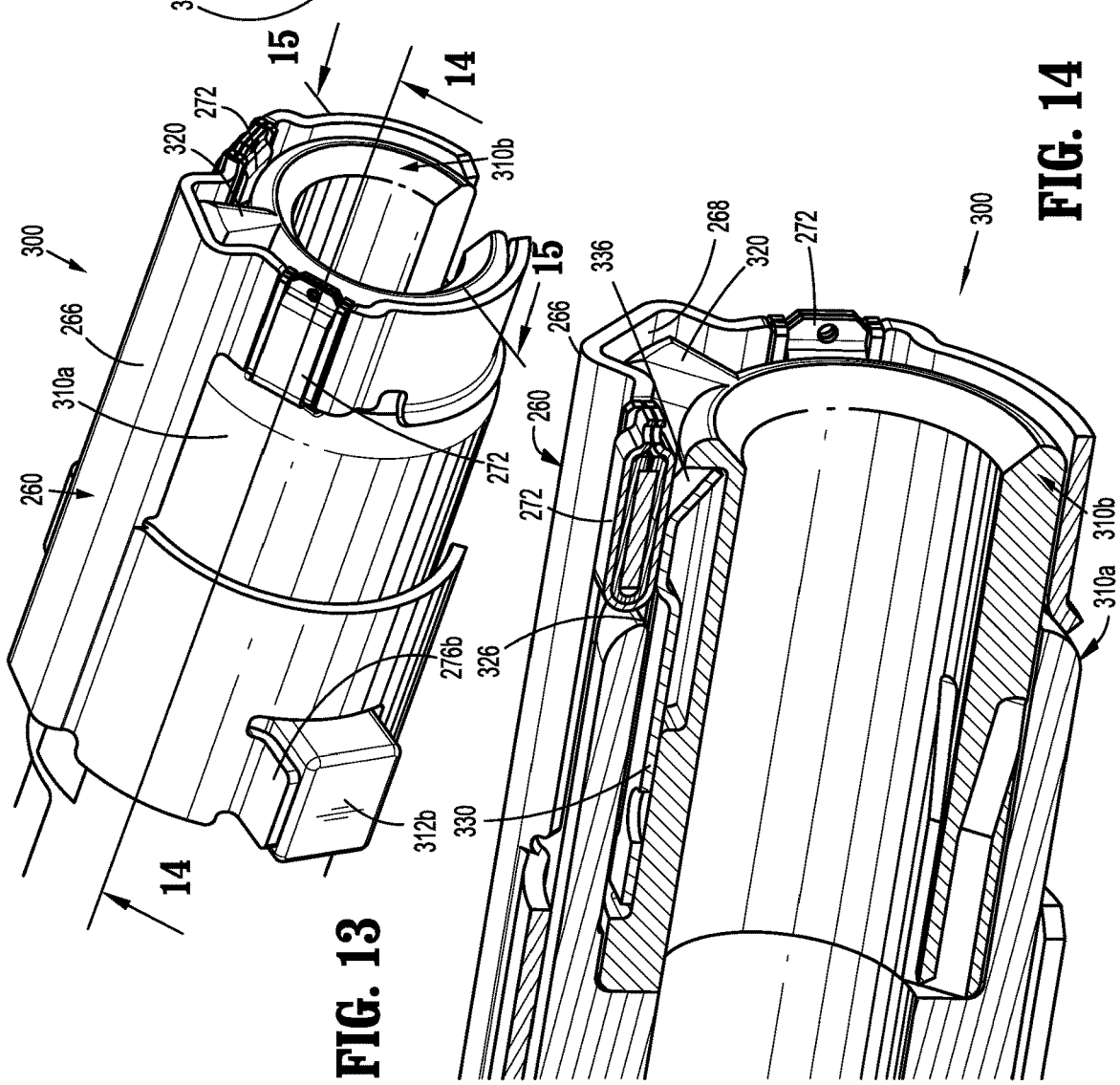
FIG. 13
FIG. 14
FIG. 15

ADAPTER ASSEMBLIES FOR INTERCONNECTING SURGICAL LOADING UNITS AND HANDLE ASSEMBLIES

CROSS-REFERENCE TO RELATED APPLICATIONS

This application claims the benefit of and priority to U.S. Provisional Patent Application No. 62/017,626, filed Jun. 26, 2014, the entire disclosure of which is incorporated by reference herein.

BACKGROUND

1. Technical Field

The present disclosure relates to adapter assemblies for use with an electromechanical surgical system and their methods of use. More specifically, the present disclosure relates to hand-held, electromechanical surgical instruments capable of detecting the presence of a loading unit and/or identifying one or more parameters of a loading unit attached to an adapter assembly.

2. Background of Related Art

Linear clamping, cutting, and stapling surgical devices may be employed in surgical procedures to resect tissue. Conventional linear clamping, cutting, and stapling devices include a handle assembly, an elongated shaft and a distal portion. The distal portion includes a pair of scissors-styled gripping members, which clamp about the tissue. In this device, one or both of the two scissors-styled gripping members, such as the anvil portion, moves or pivots relative to the overall structure. The actuation of this scissoring device may be controlled by a grip trigger maintained in the handle.

In addition to the scissoring device, the distal portion may also include a stapling mechanism. One of the gripping members of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

A need exists for various types of adapter assemblies that communicate relevant information to a handle assembly upon a proper engagement of a loading unit with a handle assembly.

SUMMARY

The present disclosure relates to adapter assemblies for use between handle assemblies and loading units. The present disclosure also relates to mechanisms for toggling a switch of an adapter assembly for effectively communicating information about a loading unit to a handle assembly, which is coupled to the adapter assembly, upon engagement of the loading unit with the handle assembly.

According to an aspect of the present disclosure, an adapter assembly is provided. The adapter assembly includes an elongated body, a switch, a sensor link, and an annular member. The elongated body includes a proximal portion configured to couple to a handle assembly and a distal portion configured to couple to a surgical loading unit. The switch is configured to toggle in response to the surgical loading unit being coupled to the distal portion. The sensor link is disposed within the distal portion and biased toward a distal position. The sensor link is longitudinally movable between a proximal position and the distal position. The annular member is disposed within the distal portion and is rotatable between a first orientation, in which the annular member prevents distal movement of the sensor link, and a second orientation, in which the sensor link moves distally to toggle the switch.

In embodiments, the annular member may be electrically connected to the switch and the annular member may include at least one electrical contact configured to engage a corresponding electrical contact of the surgical loading unit.

In embodiments, the annular member may include a surface feature configured to interface with the surgical loading unit, such that the annular member is rotatable by the surgical loading unit. The surface feature may abut the sensor link to maintain the sensor link in the proximal position.

In embodiments, the sensor link may include a tab configured to engage the switch when the sensor link is in the distal position. The adapter assembly may further include a locking link disposed within the distal portion and have a distal end. The locking link may be resiliently biased toward a locking configuration to secure the surgical loading unit with the distal end of the locking link. The distal end of the locking link may include an extension configured for locking engagement with a lug of the surgical loading unit upon insertion and rotation of the surgical loading unit into the elongated body.

In another aspect of the present disclosure, an embodiment of a surgical instrument is provided. The surgical instrument includes a handle assembly, a surgical loading unit, and an adapter assembly. The handle assembly includes a motor and a processor configured to control the motor. The surgical loading unit has an end effector disposed at a distal end thereof. The surgical loading unit includes a memory configured to store at least one parameter relating to the surgical loading unit. The memory has a first electrical contact. The adapter assembly includes an elongated body including a proximal portion configured to couple to the handle assembly and a distal portion configured to couple to a proximal end of the surgical loading unit. The adapter assembly further includes a switch and an annular member. The switch is configured to couple the memory to the processor in response to the surgical loading unit being coupled to the distal portion. The annular member is disposed within the distal portion and electrically connected to the switch. The annular member includes a second electrical contact configured to engage the first electrical contact upon insertion of the surgical loading unit into the adapter assembly.

In embodiments, the surgical loading unit may further include an outer housing and an inner housing disposed within the outer housing. The memory may be attached to the inner housing and at least a portion of the first electrical contact is exposed.

In embodiments, the surgical loading unit may include a pair of opposing lugs disposed at a proximal end thereof. The adapter assembly may further include a sensor link disposed within the distal portion and biased toward a distal position. The sensor link may be longitudinally movable between a proximal position and the distal position. The annular member may be rotatable between a first orientation, in which the annular member prevents distal movement of the sensor link, and a second orientation, in which the sensor link moves distally into the distal position to actuate the switch. The annular member may include a surface feature configured to interface with a first one of the pair of lugs, such that the annular member is rotatable by the surgical loading unit. The sensor link may include a tab configured to engage the switch when the sensor link is in the distal position.

In embodiments, the adapter assembly may include a locking link disposed within the distal portion and having a distal end. The locking link may be resiliently biased toward a locking configuration to secure the surgical loading unit with the distal end of the locking link. The distal end of the locking link may include an extension configured for locking engagement with a second one of the pair of lugs upon insertion and rotation of the surgical loading unit into the elongated body. The annular member may include a tab configured to engage the distal end of the locking link when the locking link is in the locking configuration.

In embodiments, the at least one parameter stored by the memory may be a serial number of the loading unit, a type of the loading unit, a size of the loading unit, a staple size, a length of the loading unit, or number of uses of the loading unit.

In yet another aspect of the present disclosure, an embodiment of a surgical loading unit is provided. The surgical loading unit has a proximal portion configured for engagement with an adapter assembly of a surgical instrument and a distal portion having an end effector extending therefrom. The surgical loading unit includes a memory configured to store at least one parameter relating to the surgical loading unit. The memory includes an electrical contact and is configured to communicate to a handle assembly a presence of the surgical loading unit and the at least one parameter of the surgical loading unit upon engagement of the surgical loading unit with an adapter assembly.

As used herein, the term "toggle" is defined as a transition between a first condition, which is one of an actuated state or an unactuated state of a switch, and a second condition, which is the other of the actuated or unactuated states of the switch.

BRIEF DESCRIPTION OF THE DRAWINGS

Embodiments of the present disclosure are described herein with reference to the accompanying drawings, wherein:

FIG. 13 is a cutaway view of the loading unit of FIG. 1C inserted into the annular member shown in FIG. 3;

FIG. 14 is a cross-section of the loading unit shown in FIG. 13, taken along line 14-14;

FIG. 15 is a cross-section of the loading unit shown in FIG. 13, taken along line 14-4 and distal to line 15-15.

DETAILED DESCRIPTION

Figure 1A:
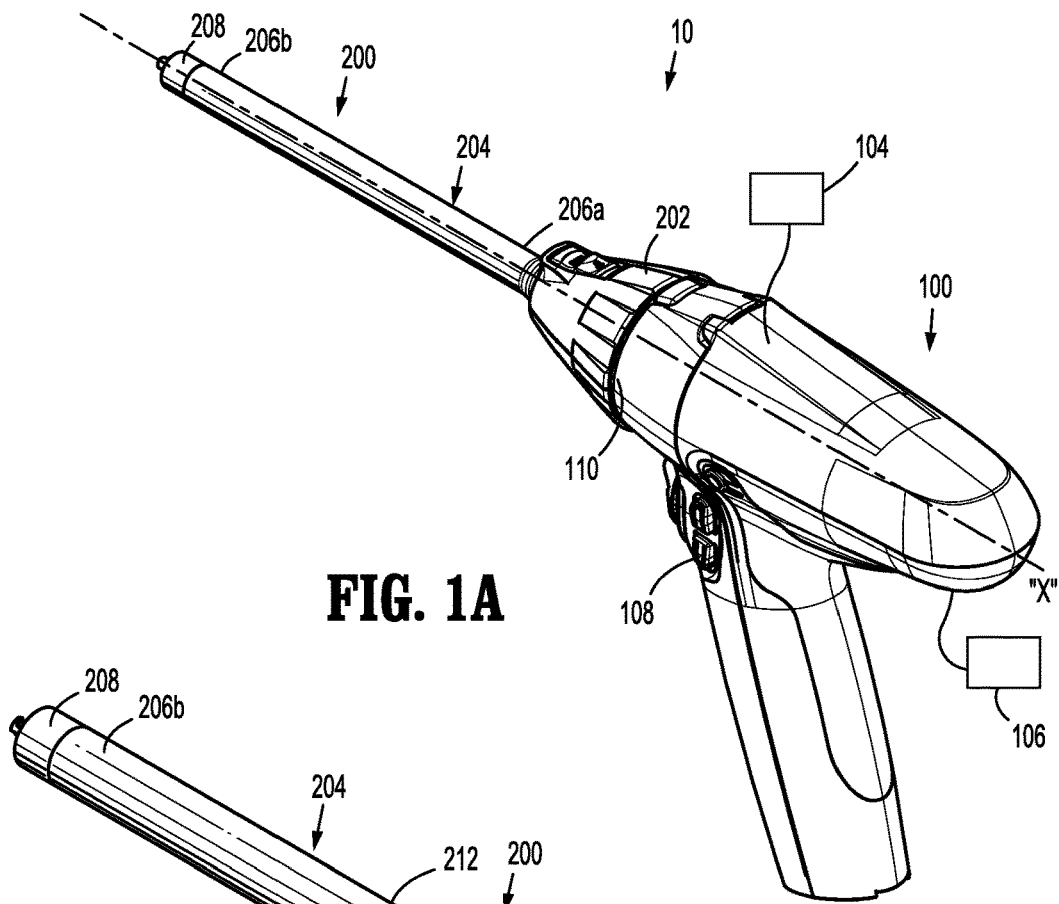
FIG. 1A is a perspective view of a hand-held, electromechanical surgical instrument, in accordance with an embodiment of the present disclosure.

Embodiments of the presently disclosed surgical instruments, surgical loading units, and adapter assemblies for electromechanical surgical devices and/or handle assemblies are described in detail with reference to the drawings, in which like reference numerals designate identical or corresponding elements in each of the several views. As used herein the term "distal" refers to that portion of the surgical instrument, adapter assembly, handle assembly, loading unit or components thereof, farther from the user, while the term "proximal" refers to that portion of the surgical instrument, adapter assembly, handle assembly, loading unit or components thereof, closer to the user.

Figure 1B:
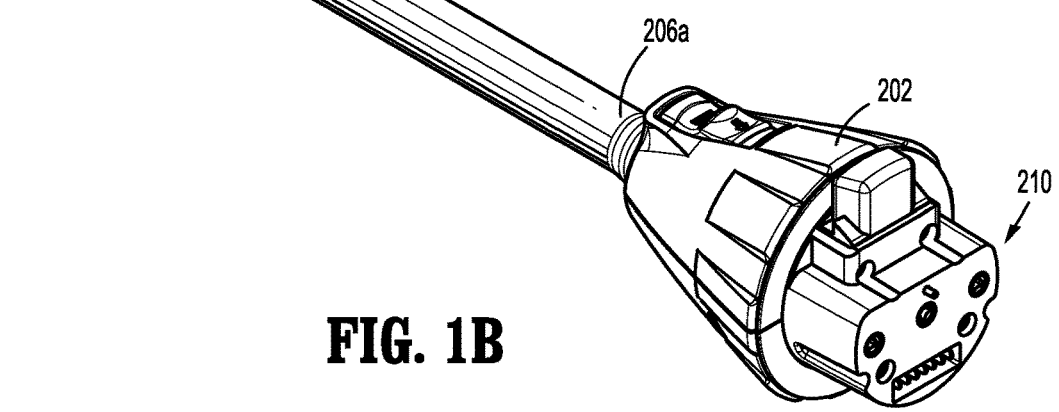
FIG. 1B is a perspective view of an embodiment of an adapter assembly of the surgical instrument shown in FIG. 1A.
Figure 1C:
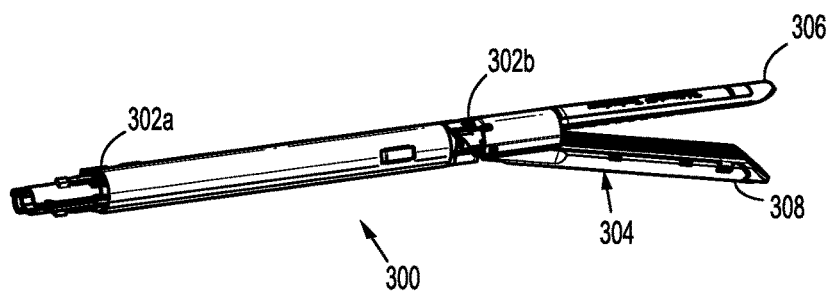
FIG. 1C is a side view of a surgical loading unit of the surgical instrument shown in FIG. 1, including an end effector attached thereto.

With reference to FIGS. 1A-C, a surgical instrument, in accordance with an embodiment of the present disclosure, is generally designated as 10, and is in the form of a powered, hand-held, electromechanical surgical instrument including a handle assembly 100 configured for selective attachment thereto with any one of a number of adapter assemblies 200, and, in turn, each unique adapter assembly 200 is configured for selective connection with any number of surgical loading units 300. Loading unit 300 and adapter assembly 200 are configured for actuation and manipulation by handle assembly 100.

Reference may be made to International Publication No. WO 2009/039506 and U.S. Patent Application Publication No. 2011/0121049, the entire contents of all of which are incorporated herein by reference, for a detailed description of the construction and operation of an exemplary electromechanical, hand-held, powered surgical instrument.

Handle assembly 100 includes one or more controllers (not shown), a power source (not shown), a processor 104, and a drive mechanism having one or more motors 106, gear selector boxes (not shown), gearing mechanisms (not shown), and the like. Processor 104 is configured to control motors 106 and to detect a presence of a loading unit, for example, loading unit 300, and/or determine one or more parameters of loading unit 300, as described herein. Handle assembly 100 further includes a control assembly 108. Control assembly 108 may include one or more finger-actuated control buttons, rocker devices, joystick or other directional controls, whose input is transferred to the drive mechanism to actuate adapter assembly 200 and loading unit 300.

In particular, the drive mechanism is configured to drive shafts and/or gear components in order to selectively move an end effector 304 of loading unit 300 to rotate end effector 304 about a longitudinal axis "X" defined by surgical instrument 10 relative to handle assembly 100, to move a cartridge assembly 308 relative to an anvil assembly 306 of end effector 304, and/or to fire a stapling and cutting cartridge within cartridge assembly 308 of end effector 304.

With continued reference to FIG. 1A, handle assembly 100 defines a nose or connecting portion 110 configured to accept a corresponding drive coupling assembly 210 of adapter assembly 200. Connecting portion 110 of handle assembly 100 has a cylindrical recess (not shown) that receives drive coupling assembly 210 of adapter assembly 200 when adapter assembly 200 is mated to handle assembly 100. Connecting portion 110 houses one or more rotatable drive connectors (not shown) that interface with corresponding rotatable connector sleeves of adapter assembly 200.

When adapter assembly 200 is mated to handle assembly 100, each of the rotatable drive connectors (not shown) of handle assembly 100 couples with a corresponding rotatable connector sleeve of adapter assembly 200. In this regard, the interface between a plurality of connectors of handle assembly 100 and a plurality of corresponding connector sleeves of the adapter assembly are keyed such that rotation of each of the drive connectors causes rotation of the corresponding connector sleeves of adapter assembly 200.

The mating of the drive connectors of handle assembly 100 with the connector sleeves of adapter assembly 200 allows rotational forces to be independently transmitted via each of the three respective connector interfaces. The drive connectors of handle assembly 100 are configured to be independently rotated by the drive mechanism.

Since each of the drive connectors of handle assembly 100 has a keyed and/or substantially non-rotatable interface with the respective connector sleeves of adapter assembly 200, when adapter assembly 200 is coupled to handle assembly 100, rotational force(s) are selectively transferred from drive mechanism of handle assembly 100 to adapter assembly 200.

The selective rotation of drive connector(s) of handle assembly 100 allows surgical instrument 10 to selectively actuate different functions of end effector 304. As discussed in greater detail below, selective and independent rotation of first drive connector of handle assembly 100 corresponds to the selective and independent opening and closing of end effector 304, and driving of a stapling/cutting component of end effector 304. Also, the selective and independent rotation of second drive connector of handle assembly 100 corresponds to the selective and independent articulation of end effector 304 about an articulation axis that is transverse to longitudinal axis "X." In particular, end effector 304 defines a second or respective longitudinal axis and is movable from a first position in which the second or respective longitudinal axis is substantially aligned with longitudinal axis "X" to at least a second position in which the second longitudinal axis is disposed at a non-zero angle with respect to longitudinal axis "X." Additionally, the selective and independent rotation of the third drive connector of handle assembly 100 corresponds to the selective and independent rotation of loading unit 300 about longitudinal axis "X" relative to handle assembly 100 of surgical instrument 10.

With continued reference to FIGS. 1A and 1B, adapter assembly 200 includes a knob housing 202 and an elongated body 204 extending from a distal end of knob housing 202. Knob housing 202 and elongated body 204 are configured and dimensioned to house the components of adapter assembly 200. Elongated body 204 may be dimensioned for endoscopic insertion. For example, elongated body 204 may be passable through a typical trocar port, cannula or the like. Knob housing 202 is dimensioned to not enter the trocar port, cannula of the like. Elongated body 204 has a proximal portion 206a attached to knob housing 202, which is configured to be attached to handle assembly 100. Elongated body 204 has a distal portion 206b configured to be coupled to proximal portion 302a of loading unit 300. Elongated body 204 further includes a distal cap 208 extending distally from distal portion 206b. Elongated body 204 further includes a cylindrical outer housing 212 and a cylindrical inner housing 214 (FIG. 2) disposed therein.

Figure 2:
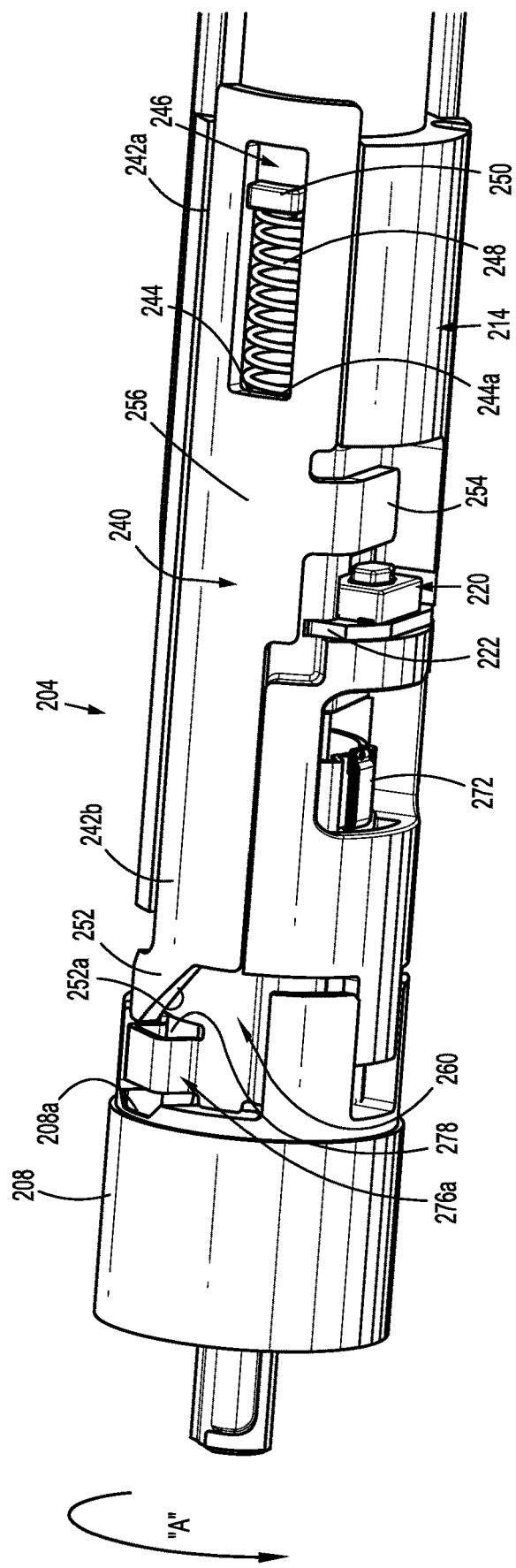
FIG. 2 is a cutaway view of a distal portion of the adapter assembly shown in FIG. 1B, without a loading unit engaged therewith.
Figure 11A:
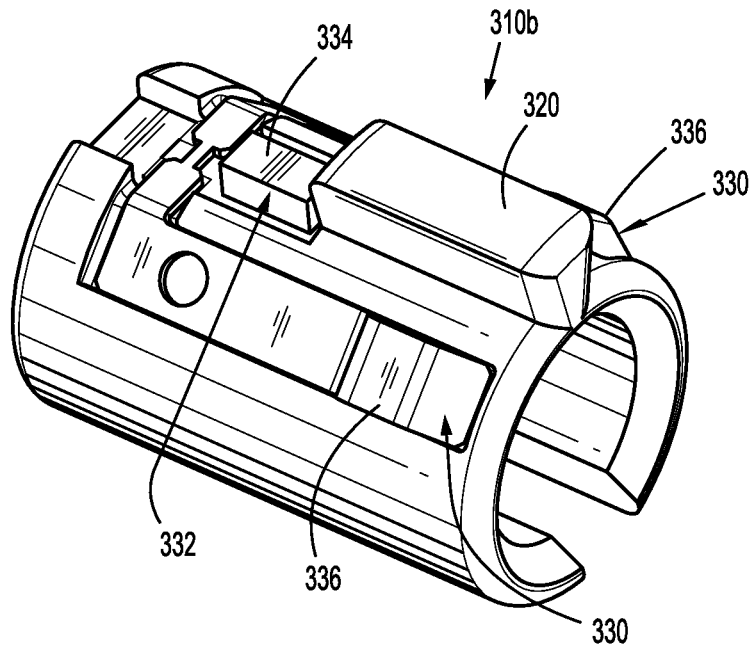
FIGS. 11A and 11B are alternate perspective views of an inner housing of the loading unit shown in FIG. 1C.
Figure 11B:
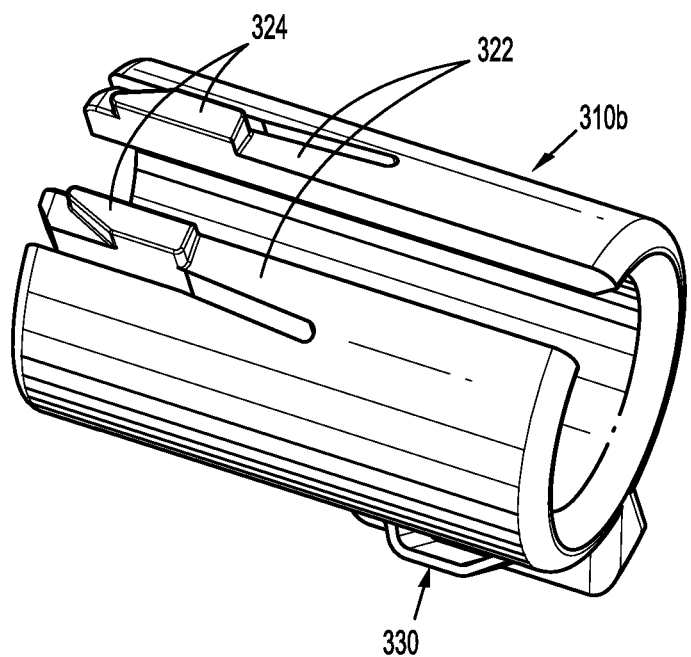

With reference to FIG. 2, adapter assembly 200 further includes a switch 220, a sensor link or switch actuator 240, an annular member 260, and a locking link 280 (see FIG. 6), each being disposed within elongated body 204 of adapter assembly 200. Switch 220 is configured to toggle in response to a coupling of loading unit 300 to distal portion 206b of elongated body 204. Switch 220 is configured to couple a memory 332 (FIG. 11A) of loading unit 300. The memory 332 may store data pertaining to loading unit 300 and is configured to provide the data to processor 104 of handle assembly 100 in response to loading unit 300 being coupled to distal portion 206b of elongated body 204. Switch 220 is disposed within distal portion 206b of inner housing 214 and is oriented in a proximal direction. In embodiments, switch 220 may be oriented in any suitable direction, such as, for example, a distal direction or a lateral direction. Switch 220 is mounted on a printed circuit board 222 that is electrically connected with processor 104 of handle assembly 100, such that upon toggling of switch 220, switch 220 communicates to handle assembly 100 that loading unit 300 is lockingly engaged to distal portion 206b of elongated body 204 or that loading unit 300 is disengaged from distal portion 206b of elongated body 204, as described in further detail below.

Figure 8:
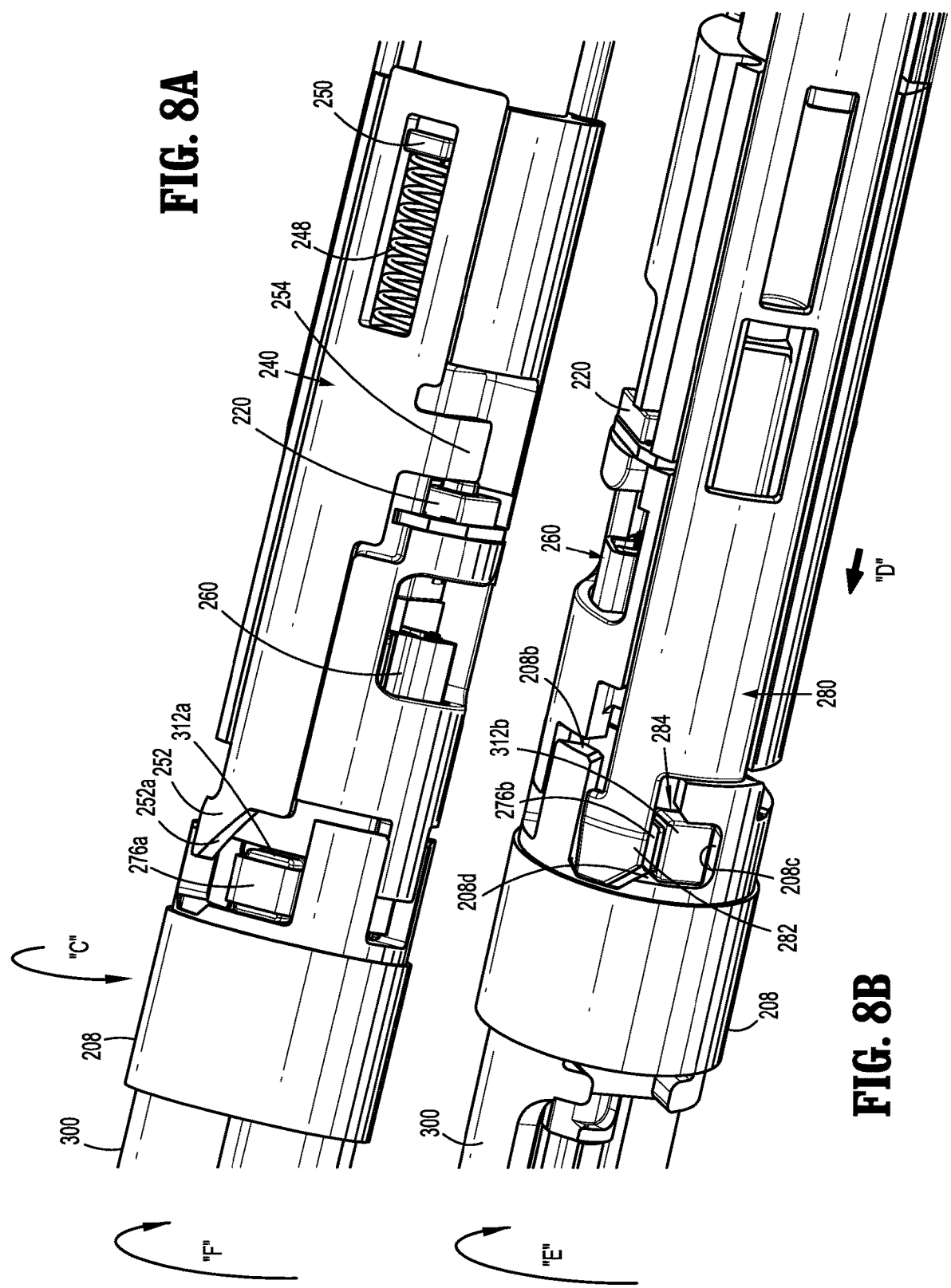
FIGS. 8A and 8B are alternate cutaway views of the distal portion of the adapter assembly shown in FIG. 2 engaged with the loading unit, illustrating the annular member in a second orientation and the sensor link in a locking configuration.
Figure 9:
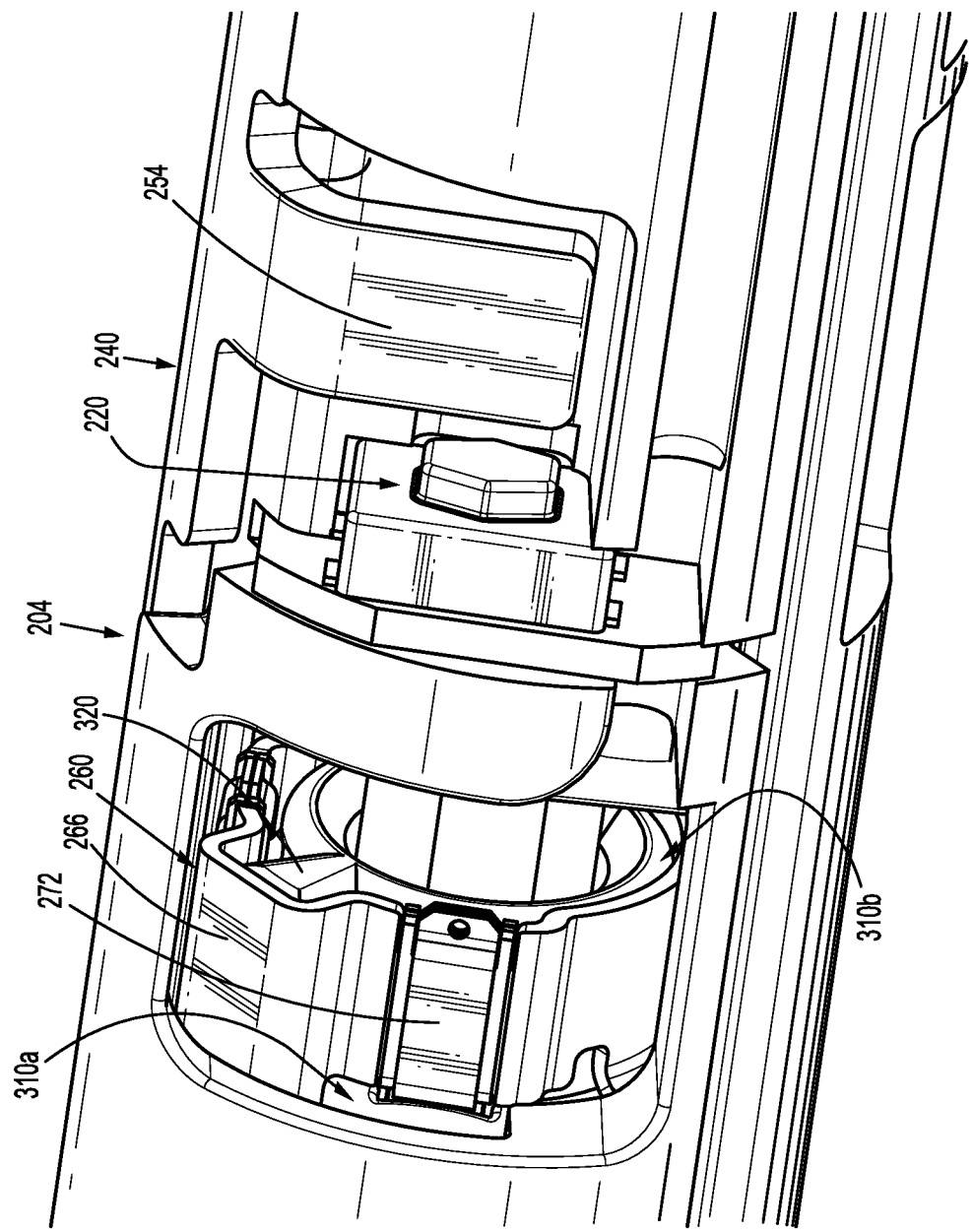
FIG. 9 is an enlarged cutaway view of the distal portion of the adapter assembly shown in FIG. 2.
Figure 10A:
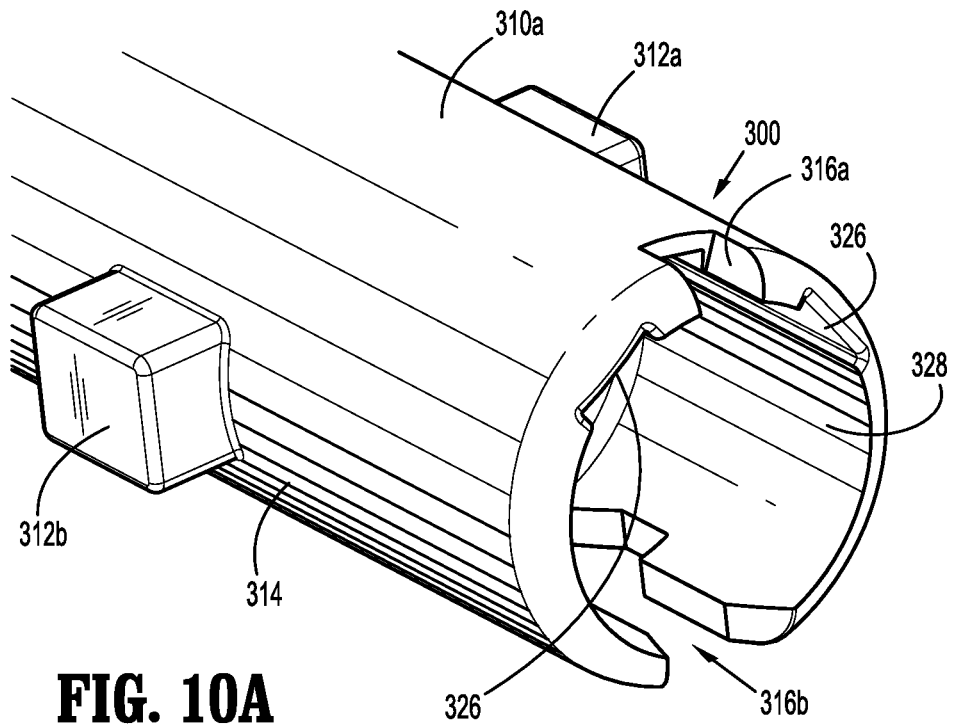
FIGS. 10A and 10B are alternate cutaway views of an outer housing of the loading unit shown in FIG. 1C.
Figure 10B:
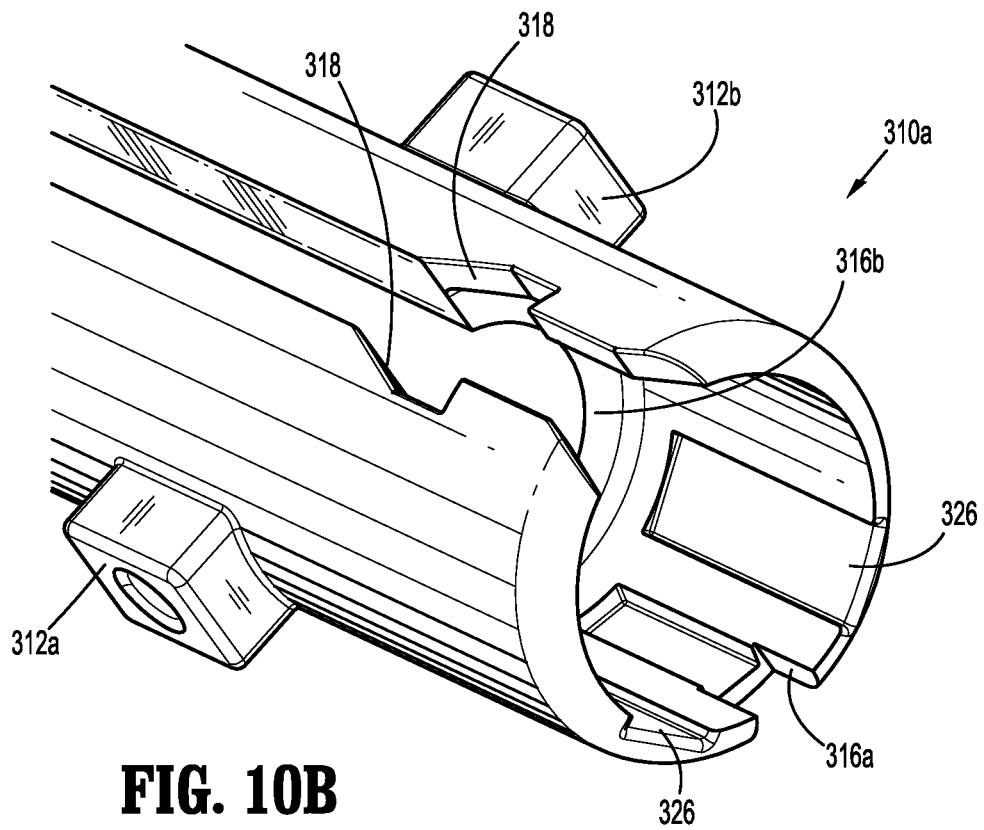

As mentioned above, adapter assembly 200 includes switch actuator 240 slidingly disposed within or along inner housing 214 of elongated body 204 and extends within distal portion 206b of elongated body 204. Switch actuator 240 is longitudinally movable between a proximal position, as shown in FIGS. 2, 5, 7A, and 7B, and a distal position, as shown in FIGS. 8A and 8B. The switch actuator 240 toggles switch 220 during movement between proximal and distal positions. In embodiments, switch actuator 240 may actuate switch 220 when in the distal position or the proximal position.

Switch actuator 240 has a proximal end portion 242a and a distal end portion 242b. Proximal end portion 242a includes an inner surface 244 that defines an elongated opening 246 having a biasing member, such as, for example, a coil spring 248 disposed therein. Coil spring 248 is secured within opening 246 between a distal end 244a of inner surface 244 and a projection 250 of inner housing 214, which projects through opening 246.

Distal end portion 242b of switch actuator 240 includes an extension 252 having a ramp portion 252a. Extension 252 is engaged to a first surface feature 276a of annular member 260 when annular member 260 is in a selected orientation relative to extension 252, such that switch actuator 240 is maintained in the proximal position. Switch actuator 240 further includes an appendage, such as, for example, a tab 254 extending from an intermediate portion 256 thereof. Coil spring 248 resiliently biases switch actuator 240 toward the distal position, as shown in FIGS. 8A and 8B, in which tab 254 actuates or depresses switch 220. In some embodiments, tab 254 actuates or depresses switch 220 when switch actuator 240 is in the distal position and unactuates switch 220 upon movement from the distal position to the proximal position.

With reference to FIGS. 2-5, adapter assembly 200 includes annular member 260, which is rotatably disposed within inner housing 214 of elongated body 204. Annular member 260 extends from a proximal end 262a to a distal end 262b and defines a cylindrical passageway 264 therethrough configured for disposal of an inner housing 310b of loading unit 300, as described in greater detail below with reference to FIGS. 9-15. Annular member 260 includes a longitudinal bar 266 defining an elongated slot 268 along a length thereof configured for sliding disposal of a fin 320 of inner housing 310b (FIG. 11A) of loading unit 300. Proximal end 262a includes a first ring 270a and distal end 262b includes a second ring 270b, spaced from first ring 270a along longitudinal bar 266. First ring 270a includes a pair of electrical contacts 272 electrically coupled to switch 220 via wires 274. Electrical contacts 272 are configured to engage corresponding electrical contacts 330 of loading unit 300, such that switch 220 and annular member 260 are capable of transferring data pertaining to loading unit 300 therebetween, as described in greater detail below. It is contemplated that a portion or portions of annular member 260 may be ring-shaped or that all of annular member 260 may be ring-shaped. The manner in which annular ring 260 captures loading unit 300 ensures that the corresponding electrical contacts 272, 330 make good electrical contacts in view of commercially achievable tolerance conditions.

Figure 3:
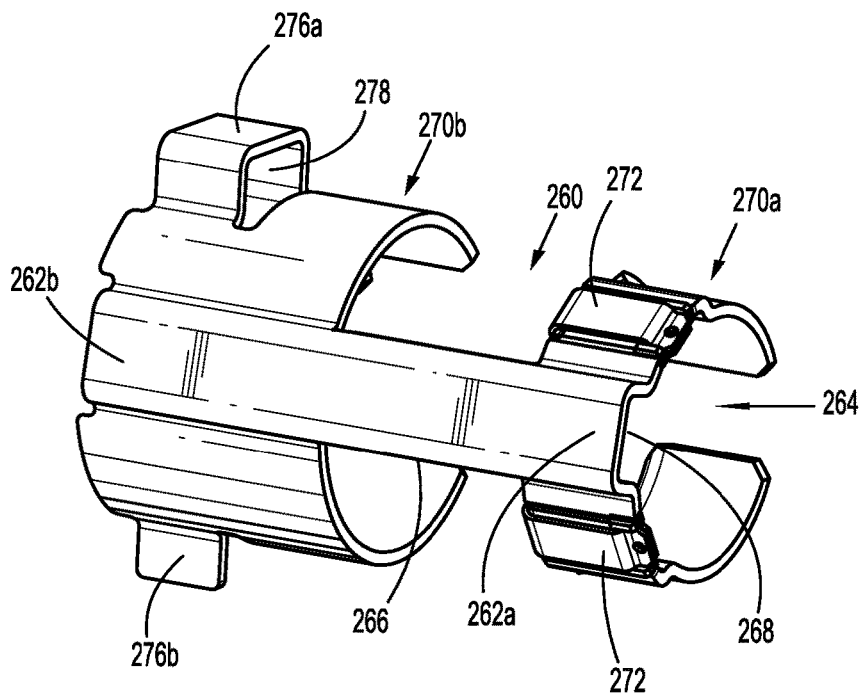
FIG. 3 is a perspective view of an annular member of the adapter assembly shown in FIG. 2.
Figure 4:
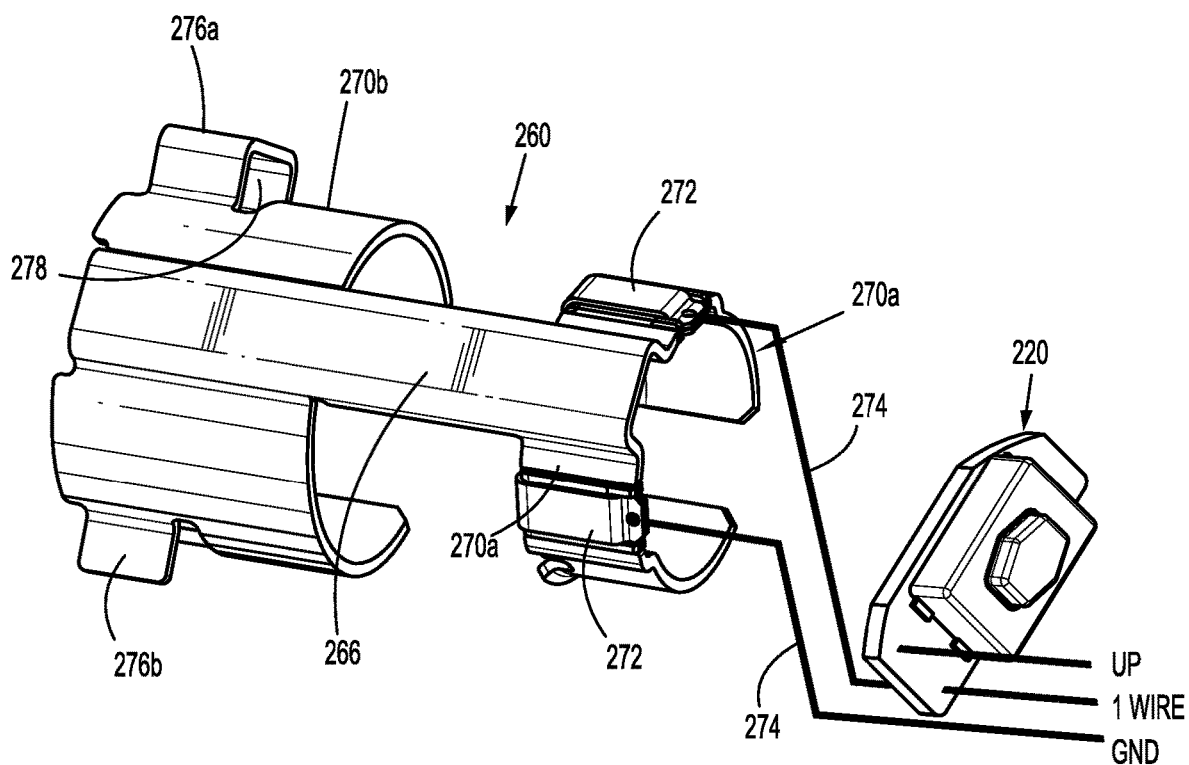
FIG. 4 is a perspective view of the annular member shown in FIG. 3 electrically connected to a switch of the adapter assembly shown in FIG. 2.
Figure 5:
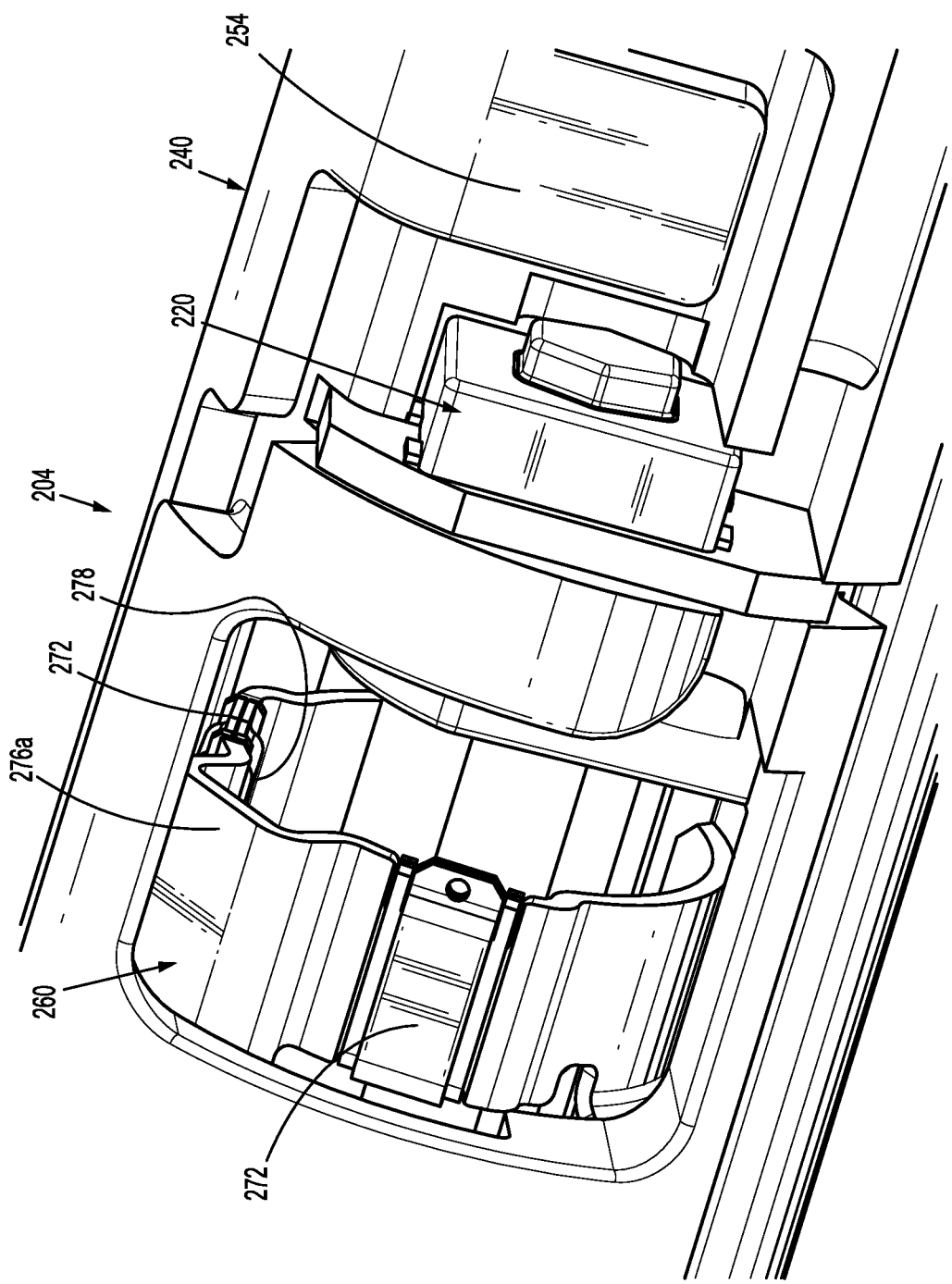
FIG. 5 is an enlarged view of the distal portion of the adapter assembly shown in FIG. 2, including the annular member and the switch assembled therein.

With specific reference to FIGS. 3 and 4, annular member 260 also includes a first surface feature 276a, and a second surface feature, such as, for example, a tab 276b, each extending from second ring 270b. Surface feature 276a of annular member 260 is configured to interface with a first surface feature or first lug 312a (FIGS. 7A and 7B) of loading unit 300, such that annular member 260 is rotatable by and with loading unit 300. Specifically, surface feature 276a defines a cavity 278 therein having a squared configuration configured for mating engagement with correspondingly shaped first lug 312a of loading unit 300. In embodiments, cavity 278 may be of various shapes, such as, for example, triangular, rectangular, circular, variable, tapered, and/or polygonal. Cavity 278 is shaped and dimensioned to capture first lug 312a (FIGS. 7A and 7B) of loading unit 300 upon insertion of loading unit 300 into adapter assembly 200, such that annular member 260 is rotatable with and by loading unit 300. Surface feature 276a of annular member 260 is also configured to abut extension 252 of switch actuator 240 to maintain switch actuator 240 in the proximal position.

Annular member 260 is rotatable between a first orientation and a second orientation. In the first orientation, as shown in FIG. 2, surface feature 276a of annular member 260 is captured between a proximal lip 208a of distal cap 208 and extension 252 of switch actuator 240. In this configuration, the surface feature 276a prevents distal movement of switch actuator 240 from the proximal position to the distal position, thereby maintaining tab 254 of switch actuator 240 out of engagement with switch 220. Accordingly, surface feature 276a of annular member 260 has a dual function for both maintaining switch actuator 240 in the proximal position, out of engagement with switch 220, and capturing first lug 312a of loading unit 300 in cavity 278 to provide an interface between loading unit 300 and annular member 260.

In use, loading unit 300 is inserted within the distal end of elongated tube 204 to mate first lug 312a of loading unit 300 with first surface feature 276a of annular member 260, as shown in FIG. 7A. Loading unit 300 is rotated, in a direction indicated by arrow "A" (FIG. 2), to drive a rotation of annular member 260 from the first orientation to the second orientation. Rotation of annular member 260 from the first orientation to the second orientation disengages surface feature 276a of annular member 260 from extension 252 of switch actuator 240 such that coil spring 248 of switch actuator 240 biases switch actuator 240 toward the distal position, in which switch 220 is toggled, as shown in FIG. 8A.

With continued reference to FIGS. 3 and 4, annular member 260 further includes a projection or tab 276b extending from second ring 270b. Tab 276b has a planar configuration and is configured to resist and/or prevent inadvertent rotation of annular member 260 within inner housing 214 when loading unit 300 is not engaged to adapter assembly 200. With specific reference to FIG. 6, when annular member 260 is in the first orientation, tab 276b is secured between a projection 208b of distal cap 208 and a distal end 282 of locking link 280. Rotation of annular member 260 from the first orientation to the second orientation is resisted and/or prevented until locking link 280 is moved to a non-locking configuration, as described below. In this way, tab 276b ensures that first surface feature 276a of annular member 260 is maintained in abutment with extension 252 of switch actuator 240 thereby maintaining switch actuator 240 in the proximal position until loading unit 300 is engaged to adapter assembly 200.

Figure 6:
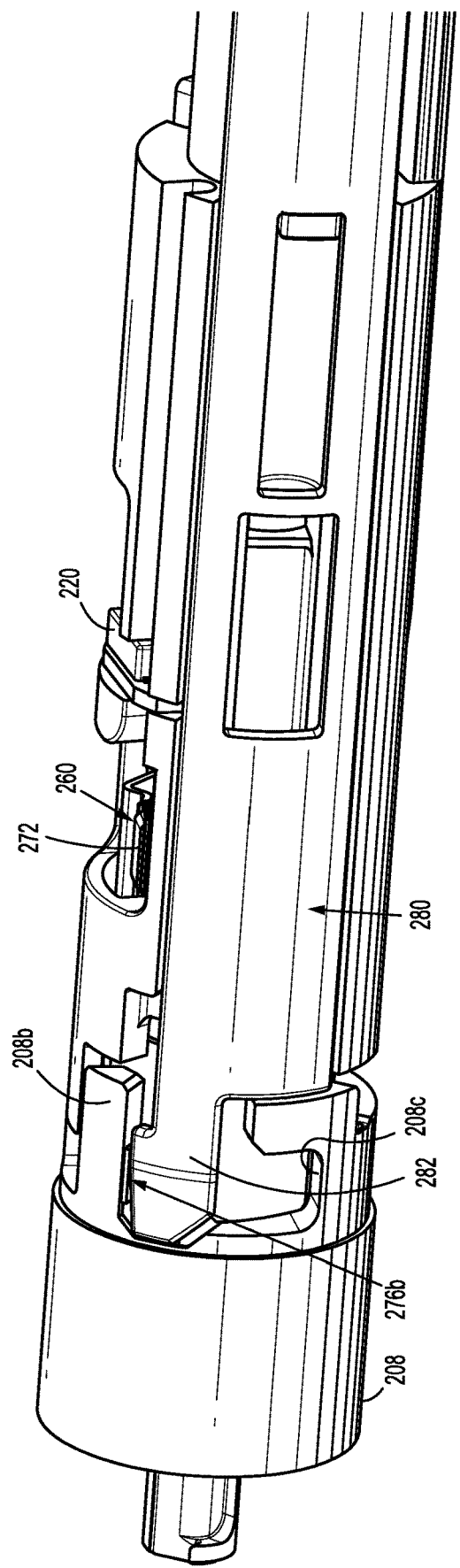
FIG. 6 is another cutaway view of the distal portion of the adapter assembly shown in FIG. 1B, without a loading unit engaged therewith.
Figure 7:
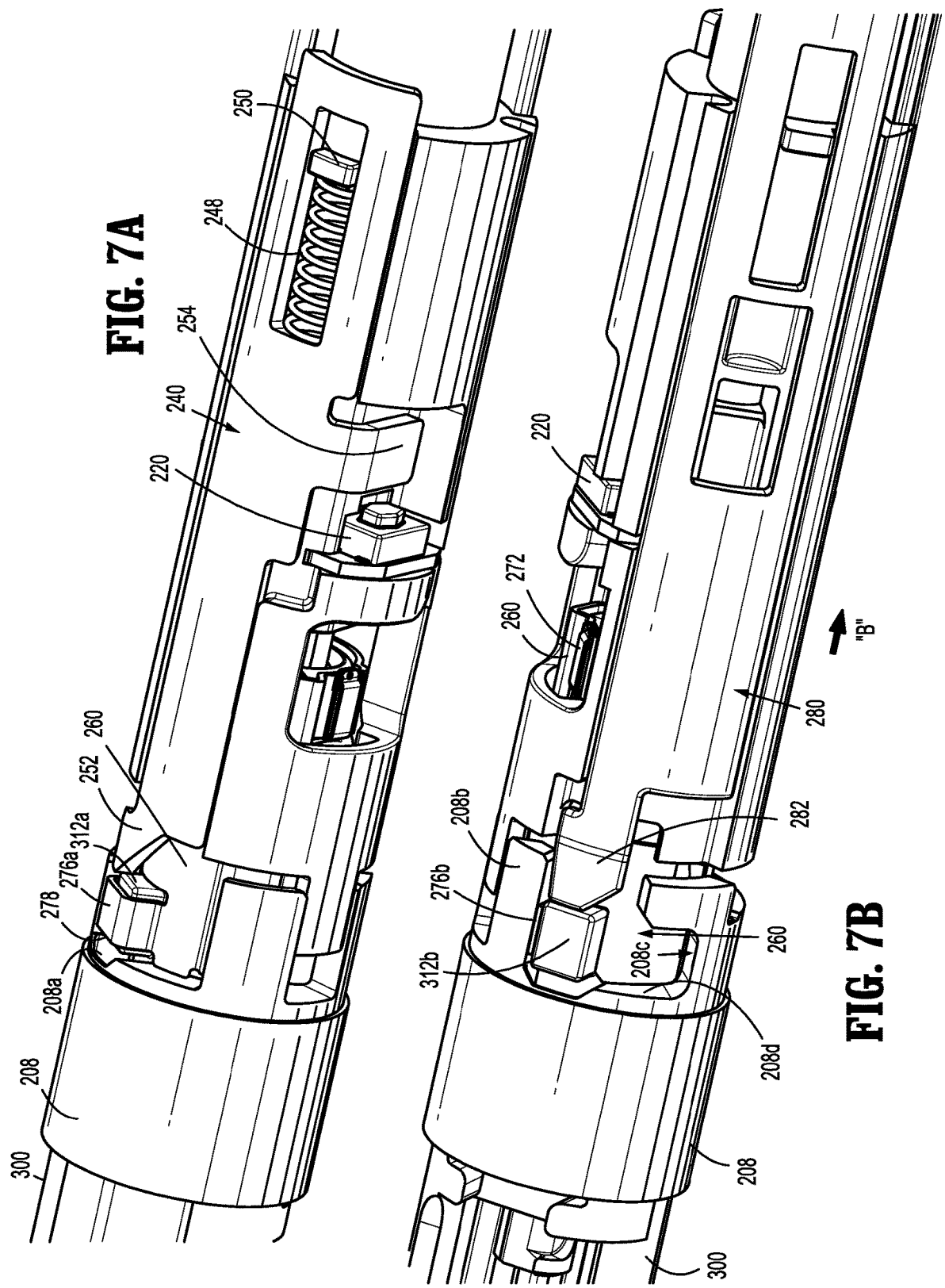
FIGS. 7A and 7B are alternate cutaway views of the distal portion of the adapter assembly shown in FIG. 2 engaged with the loading unit, illustrating the annular member in a first orientation and a sensor link in a non-locking configuration.

With reference to FIGS. 6, 7B, and 8B, adapter assembly 200 further includes locking link 280, which is disposed within distal portion 206b of adapter assembly 200. Locking link 280 is slidingly disposed within or along inner housing 214 of adapter assembly 200 and is resiliently biased toward a locking configuration, as shown in FIGS. 6 and 8B. In the locking configuration, a distal end or extension 282 of locking link 280 is engaged with distal cap 208. Extension 282 of locking link 280 is configured for locking engagement with a second surface feature, such as, for example, a second lug 312b (FIGS. 7A and 7B) of loading unit 300 upon insertion and rotation of loading unit 300 into elongated body 204. As shown in FIG. 8B, the loading unit 300 engages adapter assembly 200 and locking link 280 in the locking configuration, second lug 312b of loading unit 300 is captured in an enclosure 284 defined by extension 282 of locking link 280 and distal cap 208.

In operation, a surgical loading unit, such as, for example, loading unit 300, is inserted into distal end 206b of elongated body 204 of adapter assembly 200 to matingly engage first lug 312a of loading unit 300 within cavity 278 of surface feature 276a of annular member 260, as shown in FIG. 7A. The insertion of loading unit 300 within adapter assembly 200 also engages second lug 312b with extension 282 of locking link 280 to move locking link 280 in a proximal direction, as shown in the direction indicated by arrow "B" in FIG. 7B, to the non-locking configuration, and out of abutment with tab 276b of annular member 260. In this way, extension 282 of locking link 280 is no longer prevents annular member 260 from rotating. With loading unit 300 in this initial insertion position within adapter assembly 200, switch actuator 240 remains in the proximal position out of engagement with switch 220.

To lockingly engage loading unit 300 with adapter assembly 200, loading unit 300 is rotated, in a direction indicated by arrow "C" in FIG. 8A, to drive a rotation of annular member 260, via the mating engagement between first lug 312a of loading unit 300 and surface feature 276a of annular member 260, from the first orientation to the second orientation. The rotation of annular member 260 from the first orientation to the second orientation displaces surface feature 276a of annular member 260 away from extension 252 of switch actuator 240. With surface feature 276a out of engagement with extension 252 of switch actuator 240, switch actuator 240 moves from the proximal position, as shown in FIG. 7A, to the distal position, as shown in FIG. 8A, via coil spring 248. As switch actuator 240 moves to the distal position, tab 254 of switch actuator 240 toggles switch 220, e.g., by depressing switch 220, as shown in FIG. 8A. Depressing or actuating switch 220 communicates to handle assembly 100 that loading unit 300 is lockingly engaged with adapter assembly 200 and is ready for operation.

The rotation of loading unit 300 also moves second lug 312b of loading unit 300 into an inner groove 208c defined in distal cap 208 and out of engagement with extension 282 of locking link 280. The resilient bias of locking link 280 drives an axial translation of locking link 280, in a direction indicated by arrow "D" in FIG. 8B, to dispose locking link 280 into the locking configuration. With locking link 280 in the locking configuration, second lug 312b of loading unit 300 is captured within enclosure 284 defined by extension 282 of locking link 280 and inner groove 208c of distal cap 208. Loading unit 300 is prevented from moving distally out of enclosure 284 due to an inner ledge 208d of inner groove 208c, and is prevented from rotating, in a direction indicated by arrow "E" shown in FIG. 8B, due to extension 282 of locking link 280. Therefore, loading unit 300 is releasably, lockingly engaged to adapter assembly 200.

To selectively release loading unit 300 from adapter assembly 200, a practitioner translates or pulls locking link 280 in a proximal direction, such that extension 282 of locking link 280 is no longer blocking second lug 312b of loading unit 300 and loading unit 300 can be rotated. Loading unit 300 is rotated, in a direction indicated by arrow "F" in FIG. 8A, to move second lug 312b of loading unit 300 out of abutment with inner ledge 208d of distal cap 208. The rotation of loading unit 300 also drives the rotation of annular member 260 from the second orientation to the first orientation via the mating engagement of first lug 312a of loading unit 300 and surface feature 276a of annular member 260. As annular member 260 rotates, surface feature 276a rides along ramp portion 252a of extension 252 of switch actuator 240 to drive switch actuator 240 in a proximal direction until annular member 260 is in the first orientation and switch actuator 240 is in the proximal position, out of engagement with switch 220. Upon tab 254 of switch actuator 240 disengaging switch 220, switch 220 is toggled, which communicates to the handle assembly 100 that loading unit 300 is no longer lockingly engaged with adapter assembly 200 and not ready for operation.

To fully disengage loading unit 300 from adapter assembly 200, loading unit 300 is axially translated, in a distal direction, through distal cap 208, and out of elongated body 204 of adapter assembly 200. It is contemplated that upon handle assembly 100 detecting that loading unit 300 is not lockingly engaged to adapter assembly 200, power may be cut off from handle assembly 100, an alarm (e.g., audio and/or visual indication) may be issued, or combinations thereof.

Turning to FIGS. 1 and 9-15, loading unit 300 of surgical instrument 10 will now be described in detail. Loading unit 300 has a proximal portion 302a configured for engagement with distal end 206b of elongated body 204 of adapter assembly 200. Loading unit 300 includes a distal portion 302b having an end effector 304 extending therefrom. End effector 304 is pivotally attached to distal portion 302b. End effector 304 includes an anvil assembly 306 and a cartridge assembly 308. Cartridge assembly 308 is pivotable in relation to anvil assembly 306 and is movable between an open or unclamped position and a closed or clamped position for insertion through a cannula of a trocar.

Reference may be made to U.S. Pat. No. 7,819,896, filed on Aug. 31, 2009, entitled "TOOL ASSEMBLY FOR A SURGICAL STAPLING DEVICE", the entire content of which is incorporated herein by reference, for a detailed discussion of the construction and operation of an exemplary end effector.

Loading unit 300 further includes an outer housing 310a and an inner housing 310b disposed within outer housing 310b. Outer housing 310a has a cylindrical configuration and is preferably made from an electrically conductive material. Inner housing 310b is preferably made with and insulating material. First and second lugs 312a, 312b are each disposed on an outer surface of a proximal end 314 of outer housing 310a. First lug 312a has a substantially rectangular cross-section corresponding to cavity 278 of surface feature 276a of annular member 260. Second lug 312b has a substantially rectangular cross-section corresponding to inner groove 208c of distal cap 208. Proximal end 314 of outer housing 310a is sized and dimensioned to be inserted through distal cap 208 to lockingly engage adapter assembly 200.

Outer housing 310a defines a first notch 316a and a second notch 316b in a proximal-most edge thereof. First notch 316a is configured for sliding receipt of a tapered fin 320 extending from inner housing 210b. At least a portion of fin 320 is configured for disposal in slot 268 defined in longitudinal bar 266 of annular member 260 to facilitate insertion of inner housing 310b into annular member 260. Second notch 316b is configured for a snap fit engagement with a pair of parallel, resilient fingers 322 of inner housing 310b. Second notch 316b generally has a rectangular configuration with a pair of grooves 318 defined therein. Each finger 322 has a mating part 324 configured for mating engagement with one respective groove 318 of second notch 316b. Outer housing 310a further defines a pair of channels 326 defined in an interior surface 328 thereof and disposed on either side of first notch 316a. Each channel 326 of outer housing 310a is configured for disposal of a portion of an electrical contact 330 of inner housing 310b, as described in greater detail below.

In use, fin 320 and fingers 322 of inner housing 310b are aligned with first and second notches 316a, 316b of outer housing 310a, respectively, and inner housing 310b is axially translated within outer housing 310a, until mating parts 324 of fingers 322 are captured in grooves 318 of second notch 316b to capture inner housing 310b within outer housing 310a. In embodiments, other mating mechanisms may be utilized to couple outer and inner housings 310a and 310b. In further embodiments, the outer and inner housings 310a and 310b may be integrally formed as a single housing.

Loading unit 300 further includes a memory 332 disposed within or on inner housing 310b. Memory 332 includes a memory chip 334 (e.g., an EEPROM, EPROM, or any non-transitory storage chip) and a pair of electrical contacts 330 electrically connected to memory chip 334. Memory chip 334 is configured to store one or more parameters relating to surgical loading unit 300. The parameter may include at least one of a serial number of a loading unit, a type of loading unit, a size of loading unit, a staple size, information identifying whether the loading unit has been fired, a length of a loading unit, maximum number of uses of a loading unit, and combinations thereof. Memory chip 334 is configured to communicate to handle assembly 100 a presence of loading unit 300 and one or more of the parameters of loading unit 300 described herein, via electrical contacts 330, upon engagement of loading unit 300 with adapter assembly 200.

Figure 12A:
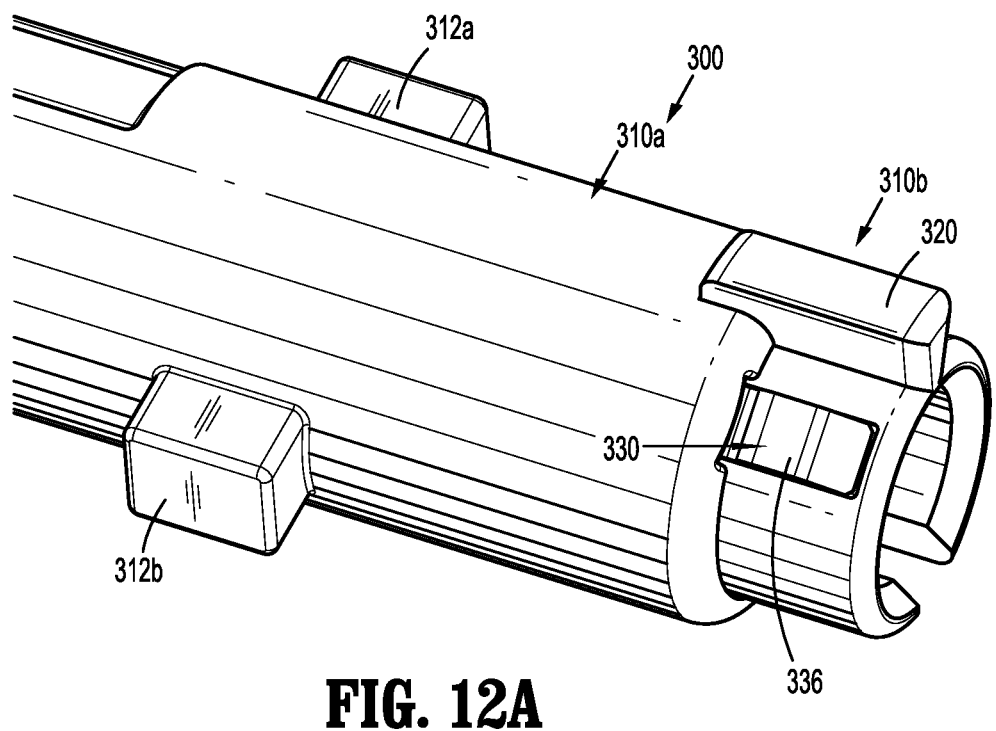
FIGS. 12A and 12B are alternate views of the loading unit shown in FIG. 1C with the inner and outer housings assembled.
Figure 12B:
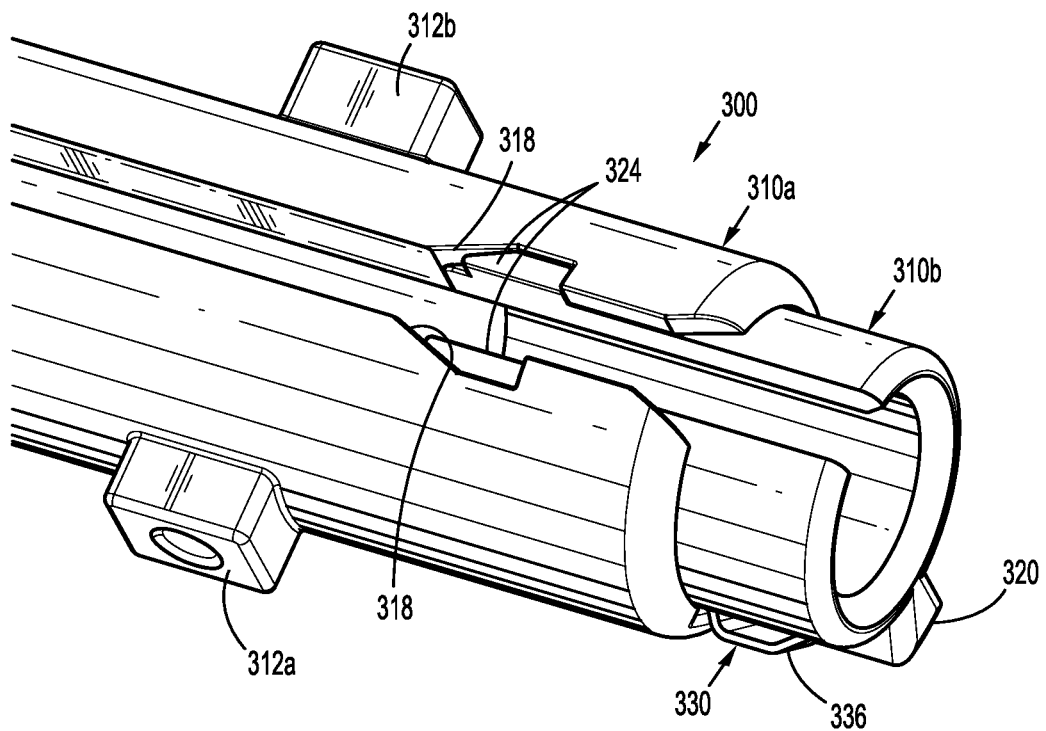

Electrical contacts 330 are disposed on an outer surface of inner housing 310b and are configured to engage electrical contacts 272 of annular member 260 upon insertion of loading unit 300 into adapter assembly 200. A proximal end of each electrical contact 330 has a bent portion 336 configured to be exposed and/or to extend beyond a proximal-most edge of outer housing 310a of loading unit 300 when inner housing 310b is secured within outer housing 310a, as shown in FIGS. 12A and 12B. Bent portions 336 of electrical contacts 330 of loading unit 330 engage electrical contacts 272 of annular member 260 upon insertion of loading unit 300 within annular member 260 of adapter assembly 200. This connection between the contacts 272 and 330 allows for communication between memory chip 334 of loading unit 300 and processor 104 of handle assembly 100. In particular, the processor 104 receives one or more parameters pertaining to loading unit 300 and/or that loading unit 300 is lockingly engaged to adapter assembly 200.

In operation, loading unit 300, with inner housing 310b disposed within outer housing 310a, is manipulated to align fin 320 of inner housing 310b and electrical contacts 330 of inner housing 310b with longitudinal bar 266 of annular member 260 and electrical contacts 272 of annular member 260, respectively. Loading unit 300 is inserted within distal end 206b of adapter assembly 200 thereby engaging first lug 312a of outer housing 310a within surface feature 276a of annular member 260 and forming a wiping contact between electrical contacts 330 of inner housing 310b and electrical contacts 272 of annular member 260, as shown in FIGS. 13-15.

As described above with reference to FIGS. 1-8, upon the initial insertion of loading unit 300 into adapter assembly 200, switch actuator 240 remains disengaged from switch 220. With switch 220 in the unactuated state, there is no electrical connection established between memory chip 334 of loading unit 300 and processor 104 of handle assembly 100. As discussed above, upon a rotation of loading unit 300, loading unit 300 lockingly engages adapter assembly 200 and switch actuator 240 toggles switch 220 to actuate switch 220. With switch 220 in the actuated state, an electrical connection is established between memory chip 334 and processor 104, through which information about the loading unit 300 is communicated to processor 104 of handle assembly 100. Upon both the actuation of switch 220 and the formation of a wiping contact between electrical contacts 330 of inner housing 310b and electrical contacts 272 of annular member 260, handle assembly 100 is able to detect that loading unit 300 has been lockingly engaged to adapter assembly 200 and to identify one or more parameters of loading unit 300.

While an electrical interface between loading unit 300 and handle assembly 100 is shown and described, it is contemplated that any other form or communication is within the scope of the present disclosure, for transmitting any or all of the operating parameters and/or the life-cycle information from loading unit 300 to handle assembly 200, such as, for example, wireless communication, including various radio frequency protocols such as near field communication, radio frequency identification "RFID," BLUETOOTH®, etc.

In further embodiments, as shown in FIGS. 16A-F, 17A, and 17B, electrical contacts 272 of annular member 260 can be variously configured to help reduce wear on the attachment (e.g., solder) interface between electrical contacts 272 and annular member 260 while annular member 260 is rotated between the first and second orientations.

Figure 16A:
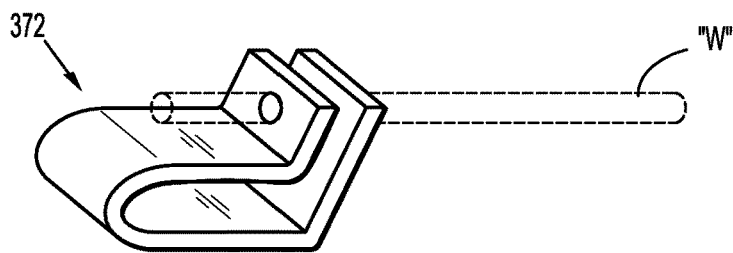
FIGS. 16A-16H are perspective views of alternate embodiments of electrical contacts of the annular member shown in FIG. 4.
Figure 16B:
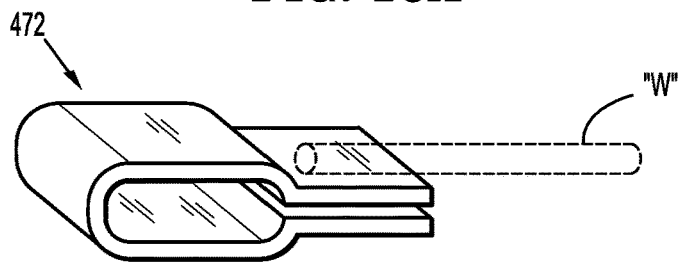
Figure 16C:
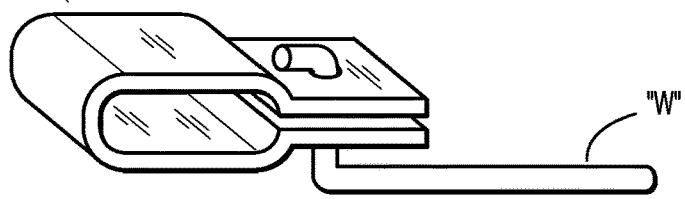

FIGS. 16A and 16B illustrate electrical contacts 372, 472 having a wire "W" soldered thereto such that wire "W" is in a linear configuration and in line with surgical instrument 10. FIG. 16C illustrates an electrical contact 572 having a wire "W" soldered thereto such that wire "W" has a bent configuration.

Figure 16D:
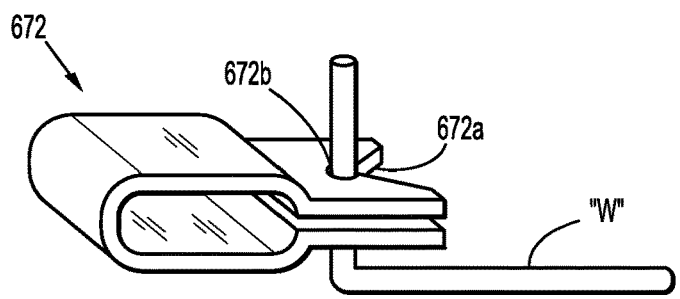
Figure 16E:
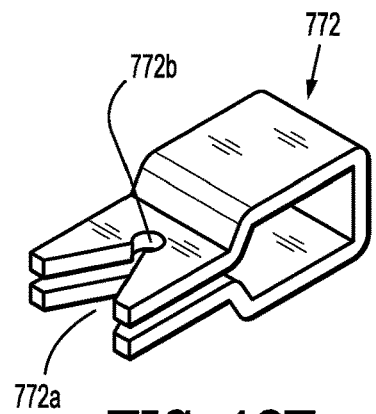
Figure 16F:
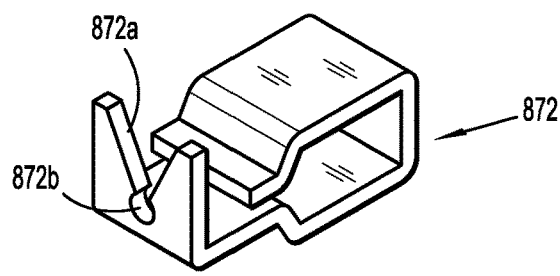

FIGS. 16D-F illustrate electrical contacts 672, 772, 872 having a key-shaped opening 672a, 772a, 872a defined therein configured for disposal of a wire "W." Key-shaped openings 672a, 772a, 872a each have a sharp edge 672b, 772b, 872b that penetrates an insulative coating of wire "W" during attachment of wire "W" to electrical contacts 672, 772, 872 to establish metal on metal contact without soldering.

Figure 16G:
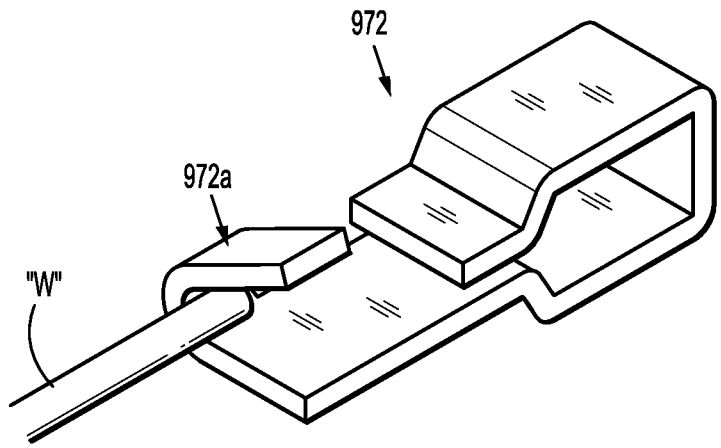
Figure 16H:
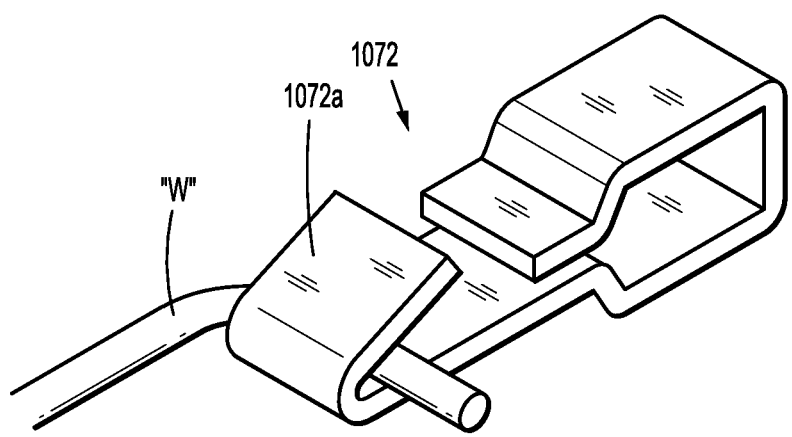

FIGS. 16G and 16H illustrate electrical contacts 972, 1072 having a bendable tab 972a, 1072a that can be crimped over a wire "W" to secure wire "W" therewith. It is contemplated that each of the above described electrical contacts are configured so that wires "W," which are soldered, crimped, and/or attached thereto in any suitable manner, can be in coaxial alignment with a longitudinal axis that extends through surgical instrument 10.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. An adapter assembly, comprising:
an elongated body including a proximal portion configured to couple to a handle assembly and a distal portion configured to couple to a surgical loading unit;
a switch configured to be toggled in response to the surgical loading unit being coupled to the distal portion of the elongated body;
a sensor link disposed within the distal portion of the elongated body and biased in a distal direction, the sensor link being longitudinally movable between a proximal position and a distal position; and
an annular member disposed within the distal portion of the elongated body, the annular member being rotatable between a first orientation, in which the annular member prevents movement of the sensor link to the distal position, and a second orientation, in which the sensor link moves distally to toggle the switch.

2. The adapter assembly according to claim 1, wherein the annular member is electrically connected to the switch and the annular member includes at least one electrical contact configured to engage a corresponding electrical contact of the surgical loading unit.

3. The adapter assembly according to claim 1, wherein the annular member includes a surface feature configured to interface with the surgical loading unit, such that the annular member is rotatable by the surgical loading unit.

4. The adapter assembly according to claim 3, wherein the surface feature abuts the sensor link to maintain the sensor link in the proximal position.

5. The adapter assembly according to claim 1, wherein the sensor link includes a tab configured to engage the switch when the sensor link is in the distal position.

6. The adapter assembly according to claim 1, further comprising a locking link disposed within the distal portion of the elongated body and having a distal end, the locking link being resiliently biased toward a locking configuration to secure the surgical loading unit to the distal end of the locking link.

7. The adapter assembly according to claim 6, wherein the distal end of the locking link includes an extension configured for locking engagement with a lug of the surgical loading unit upon insertion and rotation of the surgical loading unit into the elongated body.

8. The adapter assembly according to claim 1, wherein the annular member is configured to rotate relative to the sensor link when rotating between the first and second orientations.

9. The adapter assembly according to claim 1, wherein the annular member is configured to effect movement of the sensor link toward the proximal position upon rotation of the annular member from the second orientation toward the first orientation.

* * * * *